US00PP15993P3

(12) United States Plant Patent
de Groot

(10) Patent No.: US PP15,993 P3
(45) Date of Patent: Sep. 27, 2005

(54) HYBRID TEA ROSE PLANT NAMED 'RUIY5451'

(50) Latin Name: *Rosa hybrida*
Varietal Denomination: RUIY5451

(75) Inventor: H. C. A. de Groot, De Kwakel (NL)

(73) Assignee: De Ruiter's Nieuwe B.V., De Kwakel (NL)

( * ) Notice: Subject to any disclaimer, the term of this patent is extended or adjusted under 35 U.S.C. 154(b) by 0 days.

(21) Appl. No.: 10/406,918

(22) Filed: Apr. 4, 2003

(65) Prior Publication Data

US 2003/0217398 P1 Nov. 20, 2003

(30) Foreign Application Priority Data

May 14, 2002 (EP) ..... 2002/0749

Sep. 10, 2002 (PL) ..... O 1349

(51) Int. Cl.[7] ..... A01H 5/00

(52) U.S. Cl. ..... Plt./136

(58) Field of Search ..... Plt./130, 136, 138, Plt./139

(56) References Cited

U.S. PATENT DOCUMENTS

PP10,927 P * 6/1999 Pouw ..... Plt./130

* cited by examiner

*Primary Examiner*—Howard J. Locker
(74) *Attorney, Agent, or Firm*—Christie, Parker & Hale, LLP

(57) ABSTRACT

A new and distinct hybrid tea rose plant having attractive large flowers.

1 Drawing Sheet

Botanical classification: *Rosa hybrida.*
Varietal denomination: 'RUIY5451'.

BACKGROUND OF THE INVENTION

The present invention relates to a new and distinct variety of rose plant of the hybrid tea rose class, which was created by crossing an undistributed, unpatented seedling as seed parent with the variety known as 'Pannaran' as pollen parent (U.S. Plant Pat. No. 10,927). The varietal denomination of this new rose is named 'RUIY5451'.

SUMMARY OF THE INVENTION

Among the novel characteristics possessed by this new variety which distinguishes it from its parents and all other varieties of which I am aware are its flower color.

Asexual reproduction by propagation by grafting and by vegetative cuttings of the new variety as performed in De Kwakel, The Netherlands shows that the foregoing and other distinguishing characteristics come true to form and are established and transmitted through succeeding propagation.

COMPARISON WITH PARENTS

The new variety differs from its parents in flower color, inasmuch as the flowers of 'RUIY5451' are orange red and flowers of the seed parent are cream and light pink and flowers of the pollen parent are pink blend with apricot tones.

BRIEF DESCRIPTION OF THE ILLUSTRATION

The accompanying illustration shows a typical specimen of the new variety depicted in color as nearly true as is reasonably possible to make the same in color illustrations of this character.

In the illustration, 1, 2, 3 and 4 show the foliage; 5 shows a stem portion; 6, 7, 8 and 9 show a bud and blooms at different stages of development; and 10, 11 and 12 show the reproductive organs.

DESCRIPTION OF THE NEW VARIETY

The following is a detailed description of the new variety with color terminology in accordance with The Royal Horticultural Society Colour Chart (R.H.S.C.C.). The terminology used in color description herein refers to plate numbers in the aforementioned color chart. Phenotypic expression may vary with light availability, environmental and cultural conditions.

The following observations are made of 9-month old plants grown in a greenhouse in De Kwakel, The Netherlands during January.

Flower:

*Blooming habit.*—Continuous.

*Bud size.*—Large, about 5–6 cm. long by about 4 cm. wide.

*Form.*—Ovate.

*Color.*—When sepals first divide, orange near 33A.

*Sepals.*—Just before opening sepals are as long as the bud; color top surface near 146C to 146D; under surface near 146C to 146D and sometimes in the middle a small part near 46B; 5 sepals per flower, some sepals with small extensions, upper surface tomentum.

*Peduncle.*—Length: About 11 cm. Aspect: Smooth. Strength: Erect, strong. Color: Near 138A.

Bloom:

*Size.*—Average size when fully open is 14 cm.

*Borne.*—Singly.

*Form.*—High centered at first; becoming flat; petals remaining at first loosely rolled outward, becoming ruffled at maturity, petals reflexed before fully open.

*Petalage.*—Number of petals under normal conditions: About 25.

*Color* (*⅓ to ½ open*).—Outer petals Top surface: Near 40B. Under Surface: Near 42B. Inner Petals Top Surface: Near 40B. Under Surface: Near 42B to 42C. Base of Petals (Point of attachment): Near 13A. General tonality from a distance: Orange red.

*Color* (*fully open*).—Outer Petals Top Surface: Near 40B. Undersurface: Near 42B. Inner petals: Top surface: Near 40B. Undersurface: Near 42B. Base of Petals (Point of attachment): Near 13A. General tonality from a distance: Orange red. Color change as bloom ages.

*Petal top surface.*—Near 63B.

*Petal under surface.*—Near 63C to 63D.

*General tonality from a distance.*—Petal color becomes dull pink.

Petals:

*Texture.*—Smooth.

*Appearance.*—Inside and outside satiny; reflexing of margin is strong.

*Form.*—Shell-shaped.

*Arrangement.*—Regularly arranged, imbricated.

*Petaloids in center.*—Few, about 4; same color as petals.

*Persistence.*—Petals drop off cleanly.

*Fragrance.*—No fragrance.

*Lasting quality.*—On the plant about 18 days; as cut flower, vase life about 11 days.

Reproductive organs:

*Arrangement.*—Stamens, regularly arranged around styles.

*Color filaments.*—Yellow orange.

*Anthers.*—Near 20A and 22A.

*Pollen color.*—Brownish yellow.

*Styles.*—Uneven length about 1 cm.

*Stigmas color.*—Cream about near 11B.

*Hips shape.*—Pitcher shaped.

*Color* (*when mature*).—Light orange with green.

*Seeds.*—Some seeds protrude.

Plant:

*Form.*—Upright.

*Growth.*—Vigorous, uniform branching.

*Height attained* (*first season*).—About 200 cm.

*Foliage.*—Compound 3, 5 and 7 leaflet leaves.

*Size.*—Largest leaflets — length about 12–8 cm., width about 8–5 cm.

*Quantity.*—Usually about 14 leaves per stem.

*Color.*—New foliage Upper Side: Green near 139B with purple to bronze tinges, near 183B. Under Side: Near 178A. Old foliage Upper Side: Near 139A. Under Side: Near 137C.

*Shape.*—Elliptic.

*Texture.*—Upper Side: Weak to medium glossy. Under Side: Matte, veins are clearly visible.

*Edge.*—Serrated.

*Serration type.*—Ordinary, acuminate pieces.

*Petiole color.*—Top Surface: In center near 138B; sides near 183B. Under Side: Near 138B.

*Stipules.*—Slightly bearded.

*Length.*—About 1 cm.

*Width.*—About 0.5 cm.

*Color.*—Near 138A to 138B.

*Auricle length.*—About 4 mm.

*Width.*—About 2 mm.

*Color.*—Near 139B.

*Rachis surface.*—Top is flat. Under Side: Rounded, with some prickles.

*Resistance to disease.*—Susceptible to blackspot, mildew, and rust.

Wood:

*New shoots.*—Stem: About 10 cm.; green near 138B. Bark: Rough, with many small prickles.

*Old wood.*—Color: Green. Bark: Smooth, green near 138A, with thorns.

*Flower stem.*—Length from last cut (including peduncle): Average about 80 cm.

*Thorns.*—About 6 thorns per internode.

*On laterals from basal canes.*—Many.

*Form.*—Curved downwardly.

*Length.*—Medium, about 1 cm.

*Color* (*when young*).—Brownish purple near 187B.

*Color* (*when old*).—Greyed orange near 177B.

*Position.*—Irregular.

*Prickles.*—Normal; same color as thorns.

Winter hardiness: Not known.

Uniqueness: Very large bud size, flower color; good production, about 200 stems/$m^2$/year.

Observed plant: Grown in a 20 lt pot with a substrate of coco peat in a greenhouse in De Kwakel, The Netherlands.

*Time of year.*—January.

*Range or average day temperature.*—18° C.

*Range or average night temperature.*—16° C.

*Light level.*—5000 Lux. Photoperiodic treatments — no.

I claim:

1. A new and distinct hybrid tea rose plant of the variety substantially as shown and described.

* * * * *

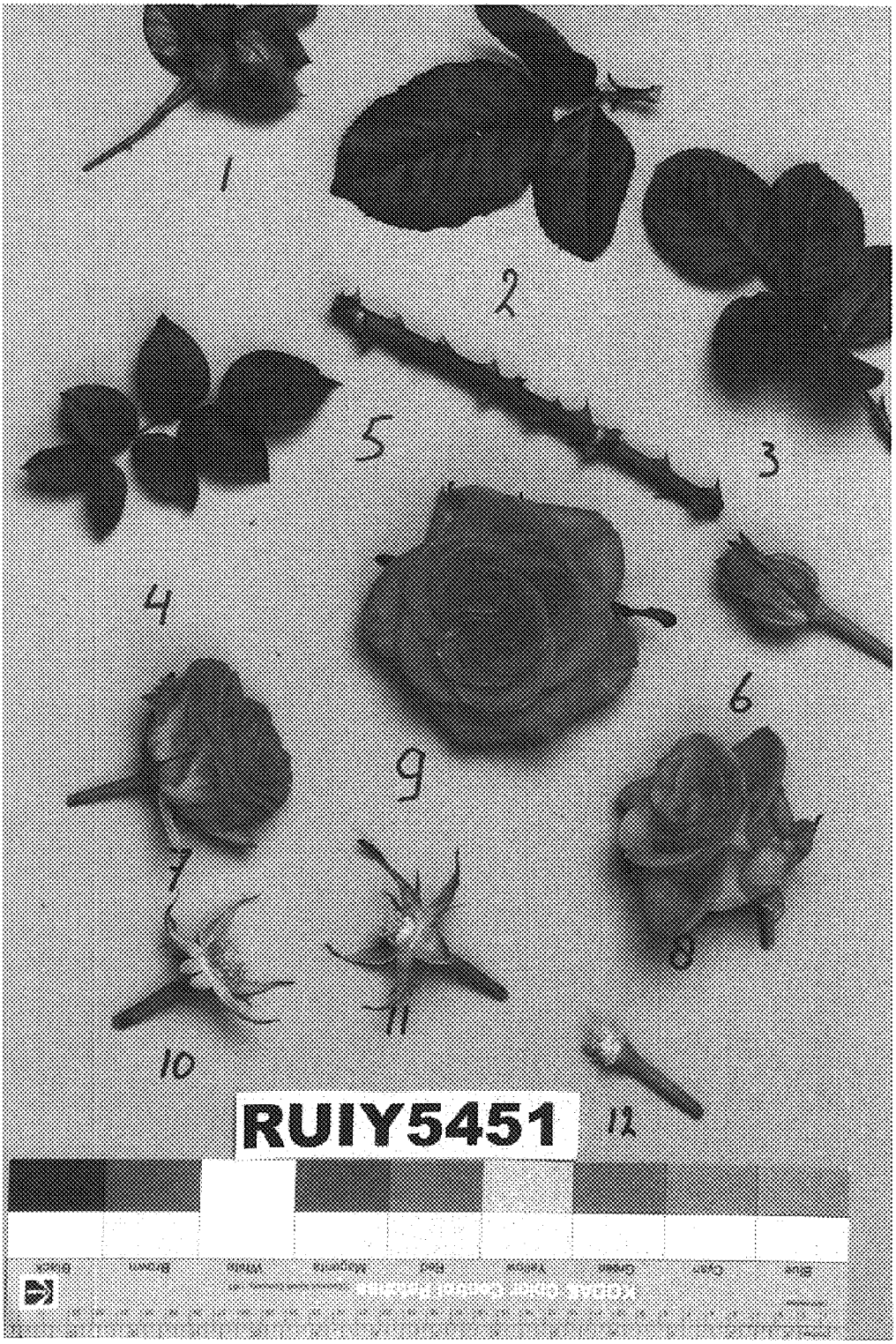
1
2
3
4
5
6
7
8
9
10
11
12
RUIY5451